Figure 1:
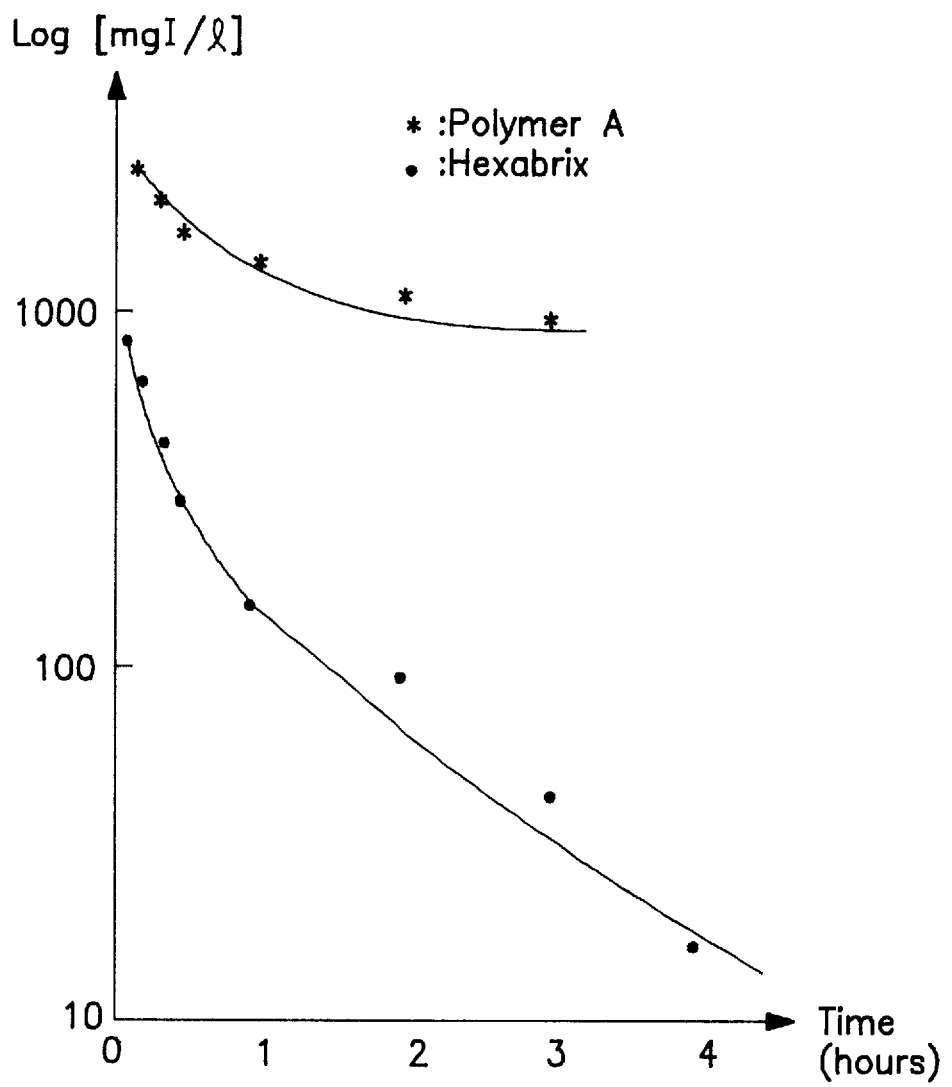

United States Patent [19]
Paris et al.

[11] Patent Number: 5,886,169
[45] Date of Patent: Mar. 23, 1999

[54] IODINATED POLYMERS, PROCESSES FOR PREPARING THEM AND THEIR APPLICATIONS AS CONTRAST MEDIA

[75] Inventors: Dominique Paris, Aulnay sous-Bois; Jean-Maxime Nigretto, L'Isle-Adam; Bruno Bonnemain, Mitry-Mory; Dominique Meyer; Didier Doucet, both of Paris, all of France

[73] Assignee: Guerbet S.A., Villepinte, France

[21] Appl. No.: 397,415

[22] PCT Filed: Feb. 12, 1988

[86] PCT No.: PCT/FR88/00077

§ 371 Date: Sep. 21, 1989

§ 102(e) Date: Sep. 21, 1989

[87] PCT Pub. No.: WO88/06162

PCT Pub. Date: Aug. 25, 1988

[30] Foreign Application Priority Data

Feb. 13, 1987 [FR] France .................................. 87 01876

[51] Int. Cl.$^6$ .............................. C08B 37/02; C07H 1/00
[52] U.S. Cl. .............................. 536/112; 536/51; 536/124
[58] Field of Search .............................. 536/112, 51, 124; 424/4, 5

[56] References Cited

U.S. PATENT DOCUMENTS

| | | | |
|---|---|---|---|
| 2,811,516 | 10/1957 | Novak | 536/112 |
| 3,702,866 | 11/1972 | Salvesen et al. | 424/5 |
| 3,852,341 | 12/1974 | Bjork et al. | 424/5 |
| 4,160,015 | 7/1979 | Wiegert et al. | 424/5 |
| 4,406,878 | 9/1983 | DeBoer | 424/5 |
| 4,455,292 | 6/1984 | Bertoni | 424/5 |

FOREIGN PATENT DOCUMENTS 2272640  12/1975  France .

OTHER PUBLICATIONS

"X–ray contrast substance", *Chemical Abstracts*, 67490b, vol. 75, 1971, By N. Sviridov et al., p. 238.

Morrison & Boyd, "Organic Chemistry" published 1975 by Allyn and Bacon, Inc. (Boston), see p. 665.

*Primary Examiner*—John Kight
*Assistant Examiner*—Everett White
*Attorney, Agent, or Firm*—Young & Thompson

[57] ABSTRACT

Iodized polymers, comprising a skeleton consisting of a dextrane onto which are grafted groups of the formula (I). Application of the these compounds as contrast products.

15 Claims, 1 Drawing Sheet

IODINATED POLYMERS, PROCESSES FOR PREPARING THEM AND THEIR APPLICATIONS AS CONTRAST MEDIA

The present invention relates to iodinated polymers which are usable in radiography as contrast media, and in particular as injectable contrast media.

Compounds used as injectable contrast media must not only absorb X-rays, but must also possess various properties and, in particular, sufficient water-solubility at physiological pH values
low toxicity,
appropriate osmolarity,
chemical stability in the body and to sterilization.

Hitherto, it was necessary to inject patients with large amounts of contrast media in order to obtain a correct diagnosis from the radiographic image. Thus, research was directed towards derivatives having more suitable osmolarity and reduced toxicity. Two new categories of media consequently appeared: ionic media having low osmolarity and non-ionic media.

More recently, an effort has been made to develop another approach, consisting in retarding the diffusion of the opacifying media in the extravascular space.

To this end, various iodinated polymers have been proposed. Thus, U.S. Pat. No. 3,852,341 describes iodinated polymers obtained by the copolymerization of a 3,5-diacylamino-2,4,6-triiodobenzene-containing acid with bifunctional compounds such as a diepoxide. These polymers are water-soluble. FR-A-2,200,018 describes related copolymers which are crosslinked and water-insoluble.

U.S. Pat. No. 4,406,878 describes an iodinated polymer which is obtained by the reaction of tetraiodophthalic anhydride with polyvinyl alcohol and crosslinking.

The present invention is directed towards the provision of new iodinated polymers which are distinguished by low osmolarity and good tolerability.

The American patent U.S. Pat. No. 2,811,516 describes an iodized polymer comprising a skeleton consisting of a dextrane onto which are grafted iodocarboxymethyl groups.

The subject of the present invention is iodinated polymers, characterized in that they comprise a skeleton consisting of a dextran onto which are grafted groups of formula

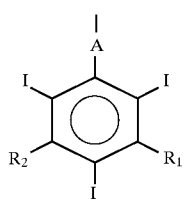

in which

A is a group forming a bridge between the dextran chain and the benzene ring, $R_1$ is a group selected from a COOH group, a COOH group salified with a pharmaceutically acceptable base and the groups of the formulae and

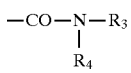

and

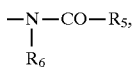

and $R_2$ is a group chosen from the groups of the formulae and

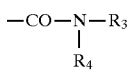

and

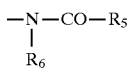

in which formulae $R_3$ and $R_5$ are selected from $C_1$ to $C_6$ alkyl, $C_1$ to $C_6$ hydroxy-alkyl, $C_1$ to $C_6$ polyhydroxyalkyl, $(C_1-C_6)$ alkoxy $(C_1-C_6)$ alkyl and $(C_1-C_6)$alkoxy $(C_1-C_6)$ hydroxyalkyl groups, $R_4$ and $R_6$ are selected from a hydrogen atom and $C_1$ to $C_6$ alkyl, $C_1$ to $C_6$ hydroxyalkyl, $C_1$ to $C_6$ polyhydroxyalkyl, $(C_1-C_6)$ alkoxy $(C_1-C_6)$ alkyl and $(C_1-C_6)$ alkoxy $(C_1-C_6)$ hydroxyalkyl groups, it being possible for $R_3$ to be, in addition, a group of formula

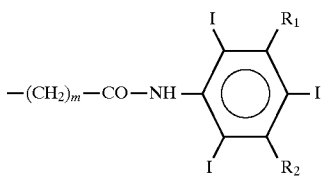

m being an integer from 1 to 6, and $R_1$ and $R_2$ having the meaning given above.

The dextran which acts as a support for the triiodobenzene groups is a polymer generally obtained from sucrose by the action of *Leuconostoc mesenteroides*.

Dextrans are polymers consisting of α-D-glucose units. The glycosyl units of the chains are linked essentially via 1→6 linkages according to the following diagram

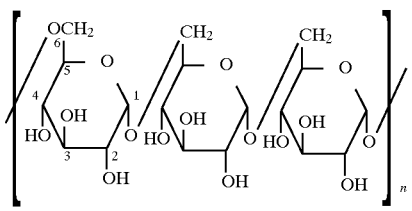

Commercial dextrans have generally undergone a partial hydrolysis followed by a fractionation to obtain polymers which are more homogeneous from the standpoint of molecular mass.

The dextrans used in the present invention can have, in particular, masses of 3,000 to 150,000, and preferably have masses of 10,000 to 100,000, in order to yield sufficiently water-soluble iodinated polymers.

The polymers according to the invention may be obtained by grafting a triiodobenzene unit onto the chain of a dextran.

Such grafting may be carried out:

either directly, by reaction of the hydroxy groups of the dextran with a reagent such as an acid chloride or acid anhydride containing a triiodobenzene group.

or indirectly, by conversion of the hydroxy groups of the dextran to more reactive groups, followed by reaction of these more reactive groups with a suitable triiodobenzene derivative.

In the first case, polymers containing ester groups are obtained according to the following scheme

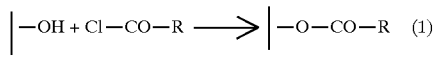

(II)

The reaction is advantageously performed by prior activation of the dextran with a base such as potassium tert-butylate, sodium hydride or 1,4-diazabicyclo[2.2.2]-octane (DABCO), or sodium alcoholates such as sodium methylate or ethylate.

The iodinated acid chloride can be, in particular, 2,4,6-triiodobenzoic acid chloride of formula

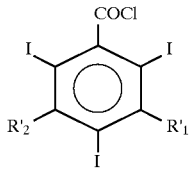

IIa in which $R'_1$ and $R'_2$ are groups chosen from a group of formula

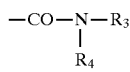

and a group of formula

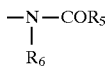

$R_3$, $R_4$, $R_5$ and $R_6$ having the meaning given above.

The reaction with an acid chloride of formula IIa leads to a polymer onto which are grafted groups

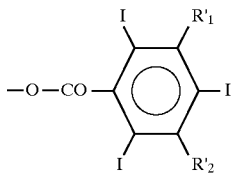

III

The reaction may be performed in a polar solvent.

In the indirect grafting reactions, in a first stage, in effect, an activation of the polymer is performed, leading to conversion of the unreactive hydroxy groups to more reactive groups capable of reacting with triiodobenzene-containing molecules having, in particular, $NH_2$ groups.

As activation reactions, the following methods may, in particular, be used:

a) Sodium periodate method This method consists in reacting sodium periodate with a dextran so as to obtain a dextran comprising units of structure

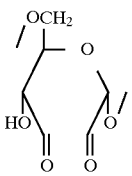

Reaction of this dialdehydodextran with an amine $RNH_2$, followed by reduction of the groups obtained, leads to a dextran onto which are grafted groups N-R, according to the following scheme

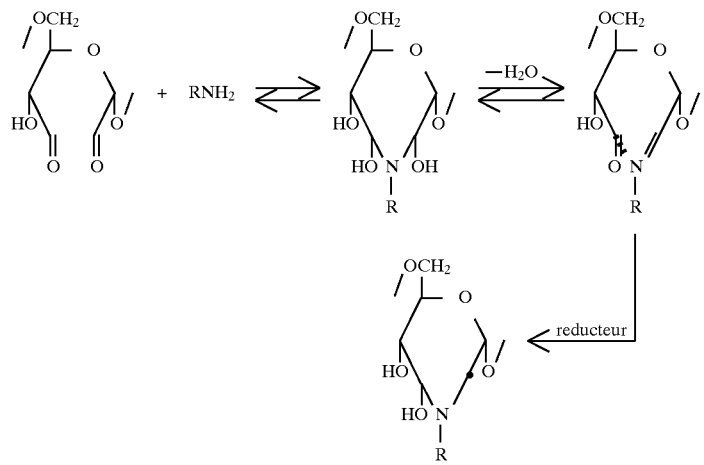

b) Tosylate or mesylate method

This method consists in reacting mesyl chloride with a dextran to yield a mesylate according to the following scheme

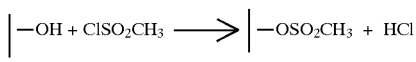

Reaction of the polymer obtained with an amine $RNH_2$ leads to a dextran onto which are grafted groups —NHR, according to the following scheme

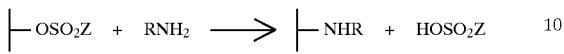

c) Monochloroacetic acid method

This method consists in reacting monochloroacetic acid in an alkaline medium according to the following reaction scheme

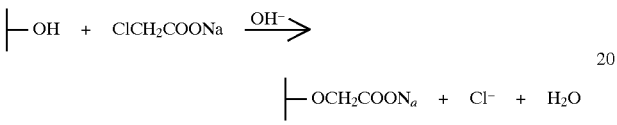

Reaction of the carboxymethyldextran obtained with an amine $RNH_2$ leads to a dextran onto which are grafted groups —$OCH_2$—CO—NHR, according to the following scheme

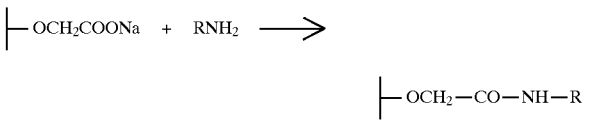

In practice, the reaction requires a coupling agent. To this end, coupling agents traditionally used for peptide synthesis, such as carbodiimides and N-ethoxycarbonyl-2-ethoxy-1,2-dihydroquinoline (EEDQ), may be used. Hexamethyldisilazane of formula $(CH_3)_3SiNHSi(CH_3)_3$ may also be used as a coupling agent.

d) Epichlorohydrin method (alkaline process)

This method consists in reacting epichlorohydrin in an alkaline medium according to the following scheme

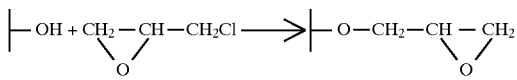

Reaction of the polymer obtained with an amine $RNH_2$ leads to a dextran onto which are grafted groups

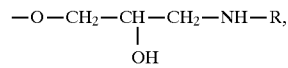

according to the following scheme

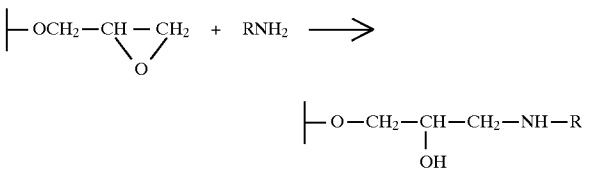

e) Epichlorohydrin method (catalytic process)

$e_1$) This method consists in reacting epichlorohydrin with dextran in the presence of $Zn(BF_4)_2$ according to the following scheme

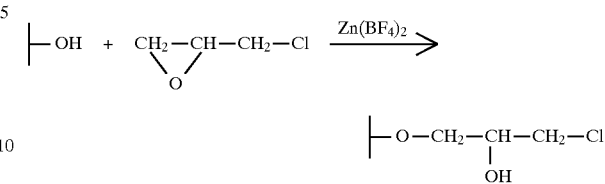

Reaction of the polymer obtained with an amine takes place according to the following scheme

$e_2$) Similarly, it is possible to react the polymer with ammonia solution according to the following scheme

An acid chloride RCOCl can then be reacted with the 3-amino-2-hydroxypropyldextran thereby obtained, leading to a structure of the following type

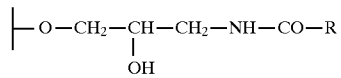

f) Succinic anhydride method

This method consists in reacting succinic anhydride with dextran in a polar solvent, using 4-dimethylaminopyridine as an acylation catalyst, according to the following reaction scheme

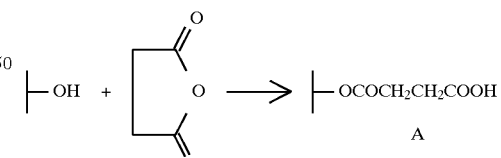

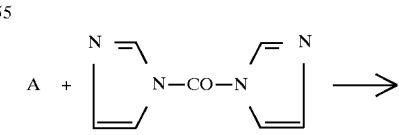

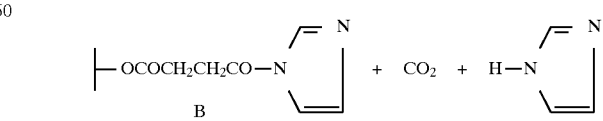

The activated polymer B can then react with an amine $RNH_2$ according to the following reaction scheme

 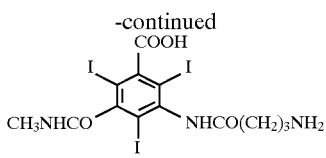

The iodinated amines used in these reactions can be, in particular, amines of formula

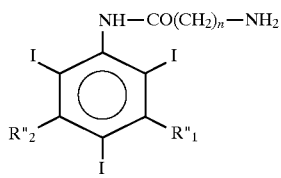

in which n is an integer from 1 to 5, $R''_1$ is a —COOH group, a COOH group salified with a pharmaceutically acceptable base or a group

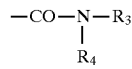

$R''_2$ is a group

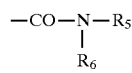

or a group

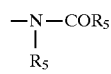

$R_3$, $R_4$, $R_5$ and $R_6$ having the meaning given above.

Amines of this type are described, in particular, in FR-A-227,640. As examples of such amines, the amines of the following formulae may be mentioned

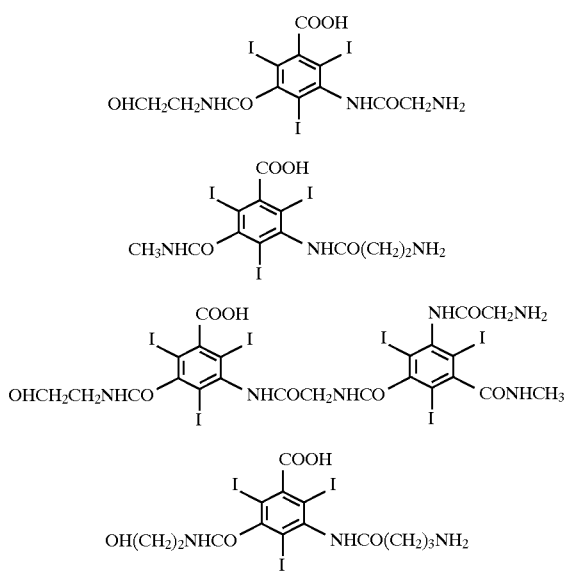

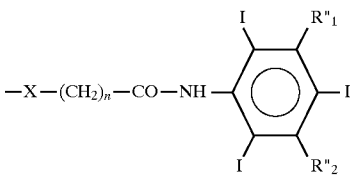

These amines lead to dextrans possessing grafted groups of formula

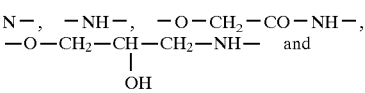

in which n, $R''_1$ and $R''_2$ have the meaning given above, and X is a group such as

$$N-, \quad -NH-, \quad -O-CH_2-CO-NH-,$$
$$-O-CH_2-CH(OH)-CH_2-NH- \quad \text{and}$$
$$-OCOCH_2CH_2-CO-NH-$$

The acid chlorides of formula IIa which are used in the method $e_2$ lead to dextrans possessing grafted groups of formula

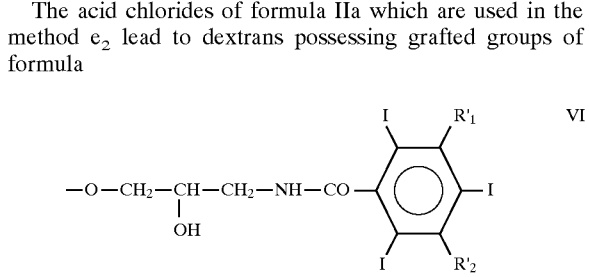

in which R' and $R''_2$ have the meaning given above.

The examples which follow illustrate the preparation of the iodinated polymers.

In these examples, the iodine contents were measured by:

*elemental analysis
*argentimetry
*UV spectroscopy

In addition, most of the products were characterized by acid-base titration in different solvents (water/water-acetone/DMSO).

All the molecular masses were measured by high pressure steric exclusion chromatography, also known as gel permeation chromatography (GPC), in comparison with the starting dextrans. The masses thus determined are designated hereinafter $M_{GPC}$.

FIG. 1 is a graph showing the iodine concentration over time, for Polymer A prepared according to Example 5 herein, versus the conventional contrast medium Hexabrix.

EXAMPLE 1

20 g of dextran (Dextran T40 of Pharmacia Fine Chemicals, stated weight average molecular mass Mw=40,000, $M_{GPC}$=27,000) are dissolved in 165 ml of 6M aqueous sodium hydroxide solution at 0° C. The solution is stirred at this temperature for 20 minutes.

41 g of monochloroacetic acid are added to the reaction medium. The temperature is then brought to 60° C. and the solution is maintained for 20 minutes at this temperature with stirring. The mixture is then cooled and thereafter neutralized to pH 7.00 by adding concentrated HCl. The product is then precipitated in 1 litre of methanol, filtered, washed and dried at 50° C. under vacuum.

24 g of carboxymethyldextran sodium salt are obtained, with a degree of substitution of 50% (determined by acid-base titration).

This same operation is repeated a second time; 26 g of carboxymethyldextran sodium salt are obtained, with a degree of substitution of 80%.

The molecular mass of the polymer obtained, determined by steric exclusion chromatography, is 47,000.

2 g of carboxymethyldextran containing 3.50 meq/g of —COONa groups (80% substitution) are dissolved in 10 ml of water and the pH of the medium is brought to 2.50 by adding concentrated HCl. Separately, 2.6 g of N-ethoxycarbonyl-2-ethoxy-1,2-dihydroquinoline (EEDQ) are dissolved in 21 ml of ethanol and gradually added to the reaction medium while stirring homogeneously. After 30 minutes, 4.6 g of iodinated amine of formula

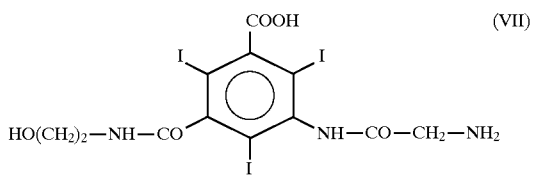

(2,4,6-triiodo-3-(N-hydroxyethylcarbamoyl)-5-acetamido-benzoic (sic) acid), dissolved in 3.5 ml of 2M sodium hydroxide, are added to the reaction medium, the pH being set at 8.50.

The reaction is left stirred at room temperature for 4 hours. The reaction medium is then evaporated under vacuum to remove the ethanol before being precipitated in 200 ml of methanol. The product is dried under vacuum at 50° C.

The content of iodine on the polymer was estimated at 6.2%.

A second binding is performed with the same amounts of reagent, to lead to an iodine content of 16%.

A third binding with 1 eq of EEDQ and 0.9 eq of amine relative to the starting carboxymethyldextran enables the iodine content to be brought to 24%. After being dried under vacuum, the polymer is redissolved in water, ultrafiltered and lyophilized.

1.5 g of iodinated carboxymethyldextran in the form of a sodium salt are obtained, with a molecular mass of 48,000 (determined by GPC). The polymer obtained possesses grafted groups of formula

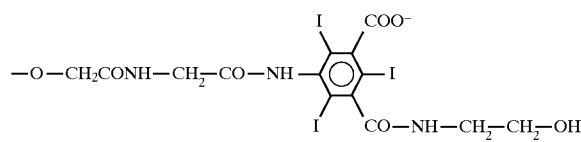

EXAMPLE 2

1.5 g of carboxymethyldextran (obtained above in Example 1) containing 3.50 meq/g of —COOH groups in the acid form are dissolved in a DMAC (20 ml)/H$_2$O (10 ml) mixture; 3.4 g of dicyclohexylcarbodiimide, dissolved in 10 ml of DNAC, are added to the above solution.

When the mixture is homogeneous, 3.6 g of iodinated amine of formula VII and 0.55 ml of triethylamine, dissolved in 10 ml of water, are added gradually. The solution is left stirred at room temperature for 24 hours and then filtered to remove the precipitated amine and dicyclohexylurea.

The filtrate is evaporated to dryness under vacuum, taken up with water and then ultrafiltered and lyophilized (the triethylamine salt being displaced by sodium hydroxide).

1.2 g of polymer containing 8% of iodine, with a molecular mass of 48,000 (determined by GPC), are obtained.

EXAMPLE 3

2 g of carboxymethyldextran (obtained in Example 1) containing 3.50 meq/g of —COONa groups, dissolved in 5 ml of water, and 1.5 g of iodinated amine of formula VII, dissolved in 20 ml of 1N sodium hydroxide, are mixed. The pH of the medium is brought to 3.00 by adding HCl.

After 10 minutes, 1.6 g of 1-ethyl-3-(3-dimethyl-aminopropyl)carbodiimide hydrochloride are added. The pH is kept constant between 4.5 and 5.0 during the first hour of reaction.

The solution is left stirred at room temperature for 24 hours and then filtered. The filtrate is ultrafiltered and lyophilized.

1.9 g of polymer containing 15% of iodine, with a molecular mass of 54,000 (determined by GPC), are obtained.

EXAMPLE 4

The procedure is identical to Example 3, but the amine used is the following

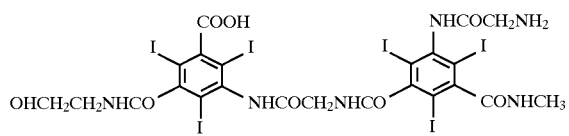

(2.9 g are reacted).

2.3 g of iodinated polymer containing 24.6% of iodine, with a molecular mass of 62,000 (determined by GPC), are obtained.

EXAMPLE 5

A carboxymethyldextran is prepared as in Example 1, but using Dextran T18 (Pharmacia Fine Chemicals, Mw=18,000, M$_{GPC}$=14,000) as the starting polymer.

Carboxymethyldextran is obtained with a degree of substitution of 70% and with a molecular mass of 29,000 (determined by GPC).

2 g of carboxymethyldextran containing 3.20 meq/g of —COCNa groups are dissolved in 10 ml of water and the pH of the medium is brought to 2.50 by adding concentrated HCl. Separately, 2.4 g of N-ethoxycarbonyl-2-ethoxy-1,2-dihydroquinoline are dissolved in 20 ml of ethanol and added gradually to the reaction medium while stirring homogeneously.

After 30 minutes, 5.9 g of iodinated amine of formula VII, dissolved in 4.5 ml of 2M sodium hydroxide, are added to the reaction medium, the pH being set at 8.50. The procedure is thereafter identical to Example 1.

The content of iodine on the polymer was estimated at 6.2%.

A second binding (1.4 eq of EEDQ and 1.1 eq of amine relative to the carboxymethyldextran) enables an iodine content of 16% to be obtained; a third binding (1.3 eq of EEDQ and 1.0 eq of amine relative to the CMD) leads to an iodine content of 24% on the polymer.

After being dried under vacuum, the polymer is redissolved in water, ultrafiltered and lyophilized.

1.9 g of iodinated carboxymethyldextran in the form of a sodium salt are obtained, with a molecular mass of 32,000 (determined by GPC).

EXAMPLE 6

A carboxymethyldextran is prepared as in Example 1, but using Dextran T10 (Pharmacia Fine Chemicals, Mw=10,000, $M_{GPC}$=7,400).

Carboxymethyldextran is obtained with a degree of substitution of 75% (3.5 meq/g) and with a molecular mass of 15,000 (determined by GPC), whereas that of the starting dextran is 7,400.

2 g of carboxymethyldextran containing 3.35 meq/g of —COONa groups are dissolved in 10 ml of water and the pH of the medium is brought to 2.50 by adding concentrated HCl. Separately, 2.5 g of N-ethoxycarbonyl-2-ethoxy-1,2-dihydroquinoline are dissolved in 20 ml of ethanol and added gradually to the reaction medium while stirring homogeneously.

After 30 minutes, 4.6 g of iodinated amine of formula VII, dissolved in 3.5 ml of 2M sodium hydroxide, are added to the reaction medium, the pH being set at 8.50.

The procedure is thereafter identical to Example 1.

The content of iodine on the polymer is estimated at 13%.

A second binding (1.4 eq of EEDQ and 0.9 eq of amine relative to the carboxymethyldextran) enables an iodine content of 22% to be obtained; a third binding (1.0 eq of EEDQ and 1.0 eq of amine relative to the carboxymethyldextran) leads to an iodine content of 26% on the polymer.

After being dried under vacuum, the polymer is redissolved in water, ultrafiltered and lyophilized.

1.8 g of iodinated carboxymethyldextran in the form of a sodium salt are obtained, with a molecular mass of 15,000 (determined by GPC).

EXAMPLE 7

0.25 g of carboxymethyldextran (obtained in Example 1) containing 3.50 meq/g of —COOH groups present in the acid form are dissolved in 10 ml of dimethylformamide, and 3 ml of hexamethyldisilazane are then added. The reaction medium is brought to 100° C. for 16 hours and the latter is then evaporated and taken up twice in DMF.

1.4 g of iodinated amine of formula VII are then added, and the heating is brought to 50° C. for 6 hours. After being cooled, the reaction medium is diluted in 100 ml of water. After 1 hour, the medium is concentrated and then precipitated in methanol.

After being dried under vacuum, the polymer is redissolved in water, ultrafiltered and lyophilized.

0.2 g of iodinated carboxymethyldextran in the form of a sodium salt, with an iodine content of 19.8% and a molecular mass of 48,000 (determined by GPC), is obtained.

EXAMPLE 8

2 g of carboxymethyldextran containing 3.20 meq/g of —COONa groups (obtained from dextran of Mw 40,000) are dissolved in 10 ml of water and the pH of the medium is brought to 2.50 by adding concentrated HCl. Separately, 2 equivalents of N-ethoxycarbonyl-2-ethoxy-1,2-dihydroquinoline and 1.5 eq of iodinated amine of formula VII are added according to the procedure described in Example 1.

A second binding is carried out with 1.5 eq of EEDQ and 1.5 eq of amine relative to the starting carboxymethyldextran.

1.5 g of iodinated polymer containing 35% of iodine, with a molecular mass of 50,000, are obtained.

EXAMPLE 9

3 g of dextran (Mw=40,000, MGPC=27,000) are dissolved in 30 ml of DMSO, and 7.2 g of succinic anhydride in 35 ml of DMSO are added to the above solution, as well as 1.8 g of 4-dimethylaminopyridine in solid form. The solution is stirred for 4 hours at 45° C. The reaction medium is precipitated in methanol. After being dried, it is redissolved in water and then ultrafiltered and lyophilized. 3 g of polymer are obtained, with a degree of substitution of 131%.

1 g of the polymer obtained above containing 4.87 meq/g of acid groups is dissolved in 20 ml of DMSO with 1.6 of carbonyldiimidazole.

The solution is stirred at room temperature for 30 minutes. 6 g of iodinated amine of formula VII, dissolved in 4.5 ml of 2M sodium hydroxide, are then added; the mixture is left stirred for 24 hours. The reaction medium is precipitated in methanol. After being dried, the product is redissolved in water, ultrafiltered and lyophilized.

The polymer obtained possesses a 20% iodine content.

The polymer obtained possesses grafted groups of formula

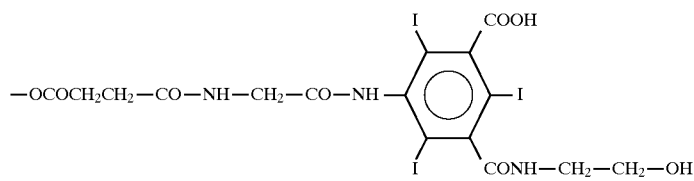

EXAMPLE 10

2 g of Dextran T 40 (Pharmacia Fine Chemicals, Mw=40,000, MGPC=27,000) are dissolved in 10 ml of anhydrous DMSO with gentle heating to 40° C.

2.8 g of potassium tert-butylate, dissolved in 10 ml of DMSO, are added, and the solution is kept stirred at 40° C. for one hour.

8 g of 2,4,6-triiodo-3-(N-methylacetamiao)-5-(N-methylcarbamoyl)benzoic acid chloride, dissolved in 20 ml of DMSO, are then introduced, and the temperature is brought to 60° C. for 5 hours.

The polymer is then precipitated in 150 ml of methanol; after being dried, it is redissolved in water, ultrafiltered and lyophilized.

1.65 g of polymer having an iodine content of 13.6%, and a molecular mass of 16,500 (determined by GPC), are obtained.

The polymer obtained possesses grafted groups of formula

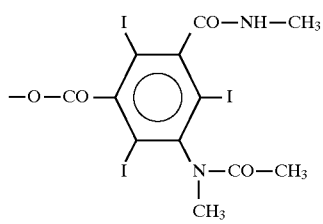

EXAMPLE 11

2 g of dextran (Mw=40,000, $M_{GPC}$=27,000) are dissolved in 10 ml of anhydrous DMSO at 40° C.; 1.4 g of potassium tert-butylate, dissolved in 5 ml of DMSO, are added, and the solution is kept stirred at 40° C. for one hour. 9.6 g of acid chloride used in Example 10, dissolved in 25 ml of DMSO, are then introduced, and the temperature is brought to 60° C. for 5 hours. The treatment is then identical to Example 10.

The content of iodine present on the polymer is equal to 10.0%; the molecular mass of the polymer is 16,000.

A second binding is carried out on the derivative obtained, with 1 eq of base and 1 eq of acid chloride relative to the starting dextran. 1.5 g of polymer containing 16.5% of iodine with a molecular mass of 14,000 are obtained.

EXAMPLE 12

2.5 g of dextran (Dextran T80, Pharmacia Fine Chemicals, Mw=80,700, $M_{GPC}$=48,000) are dissolved in 15 ml of anhydrous DMSO at 40° C.

0.75 g of sodium hydride, dispersed to a concentration of 50% in oil, are added, and the solution is kept stirred at 40° C. for 90 minutes. 11.7 g of acid chloride used in Example 10, dissolved in 20 ml of DMSO, are then introduced, and the temperature is brought to 60° C. for 5 hours.

The polymer is precipitated in 150 ml of methanol; after being dried, it is redissolved in water, ultrafiltered and lyophilized.

2.2 g of polymer containing 11.7% of iodine with a molecular mass of 28,000 (determined by GPC) are obtained.

EXAMPLE 13

2.5 g of dextran (Dextran T18, Pharmacia Fine Chemicals, Mw=18,000, $M_{GPC}$=14,000) are dissolved in 20 ml of anhydrous DMSO at 40° C.

0.75 g of sodium hydride, dispersed to a concentration of 50% in oil, are added, and the solution is kept stirred at 40° C. for 1 hour. 11.7 g of acid chloride used in Example 10, dissolved in 25 ml of DMSO, are introduced, and the temperature is brought to 60° C. for 6 hours.

After treatment, the content of iodine present on the polymer is equal to 10%; the molecular mass of the polymer is 13,000.

A second binding is carried out on the derivative obtained, with 1 eq of base.

2 g of polymer containing 13% of iodine, with a molecular mass of 11,000, are obtained.

EXAMPLE 14

4 g of dextran (Dextran T 40, Pharmacia Fine Chemicals, Mw=40,000, $M_{GPC}$=27,000) are dissolved in 60 ml of pyridine, and the temperature of the medium is brought to 70° C. 5.66 g of mesyl chloride are added slowly to the reaction medium, followed by approximately 50 ml of pyridine; the temperature is brought to 100° C.

After 2 hours 30 minutes of reaction, the solution is precipitated in 400 ml of methanol. The product is filtered off and then dried under vacuum at 50° C.

3.7 g of polymer with an 18% degree of substitution with mesylate units (%S =3.25) are obtained.

1 g of the mesylate obtained above containing 1.02 meq/g of mesyl groups is dissolved in 20 ml of water.

5 g of iodinated amine ([2,4,6-triiodo-3-carboxyl-5-(N-hydroxyethylcarbamoyl)-phenyl]carbamoylmethylamine), dissolved in 3.8 ml of 2M sodium hydroxide, are added to pH 9.60. The temperature is brought to 65° C. for 6 hours and the reaction medium is then left for 12 hours at room temperature.

The solution is precipitated in 100 ml of methanol; after filtration and drying under vacuum, the product is redissolved in water and then ultrafiltered and lyophilized.

0.6 g of polymer containing 2% of iodine with a molecular mass of 24,000 is obtained. The polymer obtained possesses grafted groups of formula

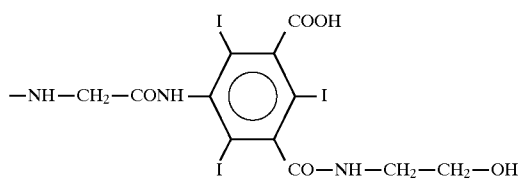

EXAMPLE 15

1 g of dextran (Dextran T10, Mw=10,000, $M_{GPC}$=7,400) is dissolved in 20 ml of 0.1M sodium acetate solution with 62 ml of 0.05M sodium periodate solution, with stirring. After 40 minutes' reaction, 0.51 g of lead nitrate is added; the solution is then filtered on a Büchner.

2.1 g of iodinated amine ([2,4,6-triodo-3-carboxy-5-(N-hydroxyethylcarbamoyl)phenyl]carbamoylmethylamine) are dissolved beforehand in 2N sodium hydroxide solution. The latter is then added gradually to the filtrate, the pH being maintained at around 7.70. The solution is stirred for 16 hours at room temperature. 0.25 g of sodium borohydride, dissolved in 2 ml of 0.1N sodium hydroxide, is then added; after two hours, the pH is brought back to around neutrality by adding hydrochloric acid and the solution is then ultrafiltered and lyophilized.

1.9 g of polymer with an iodine content of 24.2% and a molecular mass $M_{GPC}$ of 7,000 are obtained.

The polymer obtained possesses grafted groups of structure

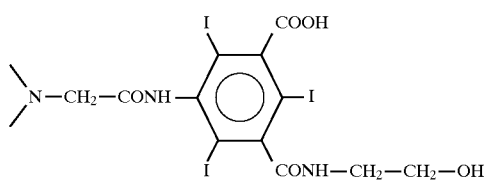

EXAMPLE 16

The procedure is identical to Example 15, but the starting dextran is Dextran T18 (Mw=18,000, $M_{GPC}$=14,000). The content of iodine on the polymer is 23%, with a molecular mass $M_{GPC}$ of 17,000.

EXAMPLE 17

The procedure is identical to Example 15, but the starting dextran is Dextran T40 (Mw=40,000, $M_{GPC}$=27,000). The content of iodine on the polymer is 24.9%, with a molecular mass of 26,000.

EXAMPLE 18

1.5 g of dextran (Dextran T18, Mw=18,000, $M_{GPC}$=14,000) are dissolved in 30 ml of 0.1M sodium acetate solution with 133 ml of 0.05M sodium periodate solution. After one hour's reaction, 1.15 g of lead nitrate are added; the solution is then filtered on a Büchner.

4.75 g of the same amine as in Example 15 are dissolved beforehand in 2N sodium hydroxide solution. The latter is then added gradually to the filtrate, the pH being maintained at around 8.00. The solution is stirred for 18 hours at room temperature. 0.4 g of sodium borohydride, dissolved in sodium hydroxide, is added; after two hours, the pH is brought back to neutrality and the solution is then ultrafiltered and lyophilized.

1.1 g of polymer with an iodine content of 29.4% and a molecular mass $M_{GPC}$ of 17,000 are obtained.

EXAMPLE 19

2.5 g of dextran (Mw=40,000, $M_{GPC}$=27,000) are dissolved in 5 ml of a 25% strength solution of zinc tetrafluoroborate and 3.5 ml of water. 17 ml of epichlorohydrin are added to the reaction medium. The mixture is stirred at 80° C. for 4 hours. The solution is then precipitated in 200 ml of methanol. The polymer obtained is dried under vacuum.

2.4 g of polymer with a 12.6% degree of substitution with chlorinated sites (%Cl=2.57) and a molecular mass of 25,000 are obtained.

The polymer obtained above is dissolved in 7 ml of ammonia solution and 7 ml of water. The reaction medium is stirred at 40° C. for 24 hours. The solution is then precipitated in 200 ml of methanol and thereafter filtered; the polymer obtained is then dried under vacuum.

2.3 g of polymer with a 12.8% degree of substitution with aminated sites (%N=1.03) and a molecular mass of 20,000 are obtained.

2.2 g of polymer containing 0.74 meq/g of amine groups and 0.17 ml of triethylamine are dissolved in a DMF/H$_2$O (10 ml:9 ml) mixture.

5.7 g of 2,4,6-triiodo-3-(N-methylacetamido)-5-(N-methylcarbamoyl)benzoic acid chloride, dissolved in 33 ml of DMF, are added gradually to the reaction medium, and the temperature is brought to 60° C. for 4 hours.

The solution is then precipitated in 200 ml of methanol and thereafter filtered. After being dried under vacuum, the polymer obtained is redissolved in water, ultrafiltered and then lyophilized.

2.0 g of polymer containing 8.1% of iodine, with a molecular mass $M_{GPC}$=20,000, are obtained. The polymer obtained possesses grafted groups of formula

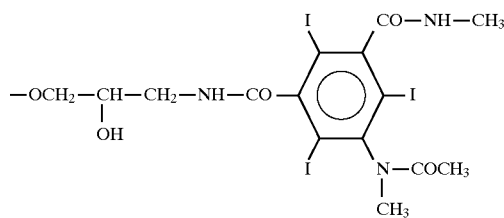

EXAMPLE 20

The procedure is identical to Example 19, but the starting dextran is Dextran T80 (Mw=80,700, $M_{GPC}$=48,000). The 3-chloro-2-hydroxypropyldextran obtained has a 14.1% degree of substitution with chlorinated sites (%Cl=2.86) and a molecular mass of 42,000.

The 3-amino-2-hydroxypropyldextran obtained has an 11.6% degree of substitution with aminated sites (%N=0.93) and a molecular mass of 30,000.

2.0 g of iodinated polymer containing 5.8% of iodine and a molecular mass $M_{GPC}$=30,000 are obtained.

EXAMPLE 21

The procedure is identical to Example 19, but the starting dextran is Dextran T18 (Mw=18,000, $M_{GPC}$= 14,000). The 3-chloro-2-hydroxypropyldextran obtained has a 16.4% degree of substitution with chlorinated sites (%Cl=3.29) and a molecular mass of 16,000. The 3-amino-2-hydroxypropyldextran obtained has a 15.0% degree of substitution with aminated sites (%N=1.20) and a molecular mass of 15,000.

2.0 g of iodinated polymer containing 9.9% of iodine and a molecular mass $M_{GPC}$=15,000 are obtained.

EXAMPLE 22

3.3 g of dextran (Mw=40,000, $M_{GPC}$=27,000) are dissolved in 5 ml of a 25% strength solution of zinc tetrafluoroborate and 3.3 ml of water. 17 ml of epichlorohydrin are added to the reaction medium. The mixture is stirred at 80° C. for 3 hours. The solution is then precipitated in 300 ml of methanol. The polymer obtained is dried under vacuum.

3.1 g of polymer with a 7% degree of substitution with chlorinated sites (%Cl=1.44) and a molecular mass of 24,000 are obtained.

0.5 g of the polymer obtained above is dissolved in a DMAC/H$_2$O (7 ml:2 ml) mixture. 2.4 g of iodinated amine of formula VII and 0.6 ml of triethylaiine, dissolved in 6 ml DMAC/3 ml water, are added to the reaction medium; the temperature is brought to 70° C. for 4 hours.

The solution is then precipitated in 150 ml of methanol and thereafter filtered; after being dried, the polymer is redissolved in water, ultrafiltered and lyophilized.

0.30 g of polymer containing 8.8% of iodine, with molecular mass $M_{GPC}$=30,000, is obtained. The polymer obtained possesses grafted groups of formula

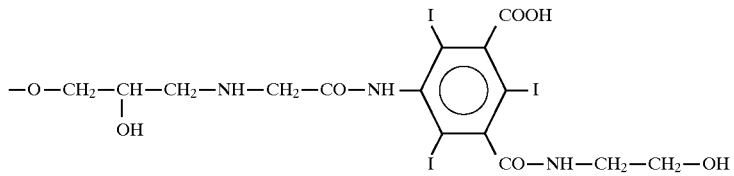

EXAMPLE 23

0.3 g of 3-chloro-2-hydroxypropyldextran (%Cl=1.44), obtained as in Example 22, is dissolved in 20 ml of DMAC. 2.8 g of amine of formula

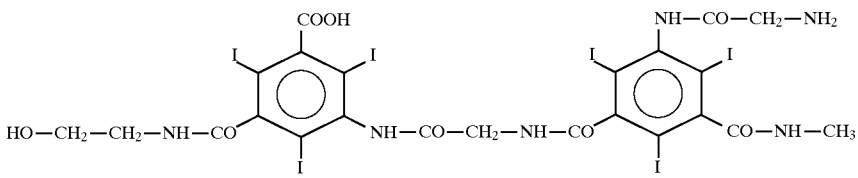

and 0.4 ml of triethylamine, dissolved in 10 ml of water, are added to the reaction medium; the temperature is brought to 60° C. for 4 hours. The solution is precipitated in 150 ml of methanol and thereafter filtered following drying; the polymer is redissolved in water, ultrafiltered and lyophilized.

0.2 g of polymer containing 8.4% of acid, with a molecular mass $M_{GPC}$=28,000, is obtained.

EXAMPLE 24

5.0 g of dextran (Mw=40,000, $M_{GPC}$=27,000) are dissolved in 8 ml of buffer which is 0.5M with respect to $CH_3COONa$ and 0.5M with respect to $CH_3COOH$; the reaction medium is brought to 70° C. At regular time intervals (t=0, t=2 hours, t=4 hours), 0.55 ml of a 50% strength solution of zinc tetrafluoroborate and 9 ml of epichlorohydrin are added. After the final addition, heating is continued for 5 hours. The solution is then precipitated in 500 ml of methanol. The polymer obtained is dried under vacuum.

4.7 g of polymer with a 27% degree of substitution with chlorinated sites (%Cl=5.2) and a molecular mass of 25,000 ($M_{GPC}$) are obtained.

The polymer obtained above is dissolved in 20 ml of a 2M $NH_4OH$/2M $NH_4Cl$ solution; the temperature is brought to 40° C. The pH is adjusted to 9.5 by adding ammonia solution.

After 48 hours' heating, the solution is precipitated in 400 ml of methanol and then filtered; the polymer obtained is thereafter dried under vacuum.

4.0 g of polymer with a 28.0% degree of substitution with aminated sites (%N=2.17) and a molecular mass of 20,000 are obtained.

4.0 g of 3-amino-2-hydroxypropyldextran are dissolved in 6 ml of water with 1.8 ml of triethylamine; the reaction medium is brought to 60° C.

16.0 g of 2,4,6-triiodo-3-(N-methylacetamido)-5-(N-methylcarbamoyl)benzoic acid chloride, dissolved in 20 ml of DMAC, are added gradually to the reaction medium, and the temperature is left at 60° C. for 24 hours. The solution is then precipitated in 400 ml of methanol and thereafter filtered.

3.0 g of polymer containing 19.7% of iodine, with a molecular mass $M_{GPC}$=20,000, are obtained. The polymer obtained possesses grafted groups of formula:

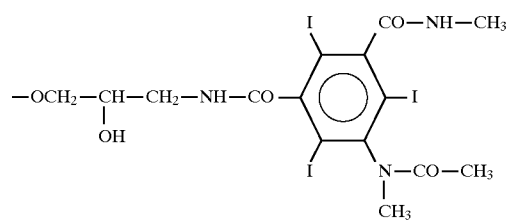

solubility: 36.8 g/100 ml, equivalent to 6.74 g $I_2$/100 ml osmolality at 37° C. (tono-metry): 288 mOsm/kg.

EXAMPLE 25

5.0 g of dextran (Mw=40,000, $M_{GPC}$=27,000) are dissolved in 8 ml of buffer which is 0.5M with respect to $CH_3COONa$ and 0.5M with respect to $CH_3COOH$; the reaction medium is brought to 70° C. At regular time intervals (t=0, t=2 hours, t=4 hours), 0.55 ml of a 50% strength solution of zinc tetrafluoroborate and 9 ml of epichlorohydrin are added. After the final addition, heating is continued for 5 hours. The solution is then precipitated in 500 ml of methanol. The polymer obtained is dried under vacuum.

4.7 g of polymer with a 32.0% degree of substitution with chlorinated sites (%Cl=6.0) and a molecular mass $M_{GPC}$ of 25,000 are obtained.

2 g of the polymer obtained above are dissolved in 5 ml of water at room temperature.

8 g of iodinated amine of formula VII, dissolved in the stoichiometric amount of sodium hydroxide, are added dropwise to the reaction medium, checking that the pH is always above 9.5.

The temperature is brought to 60° C. for 24 hours.

The solution is precipitated in 300 ml of methanol and then filtered; after being dried, the polymer is redissolved in water, ultrafiltered and precipitated in a methanol/isopropanol mixture.

1.5 g of polymer containing 22.6% of iodine, with a molecular mass $M_{GPC}$=30,000, are obtained. The polymer obtained possesses grafted groups of formula

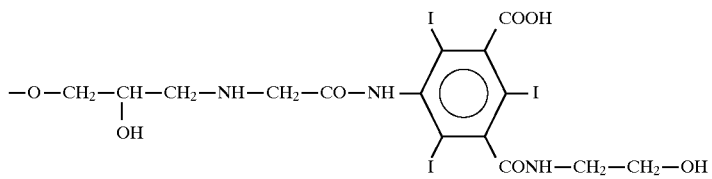

solubility: 32.5 g/100 ml, equivalent to 7.9 g $I_2$/100 ml
osmolality at 20° C.: 474 mOsm/kg.

Results relating to the water-solubilliy of the polymers thus prepared are given below:

TABLE I

Solubility in water

| Example | Solubility % m/v | % iodine in solution |
|---|---|---|
| 5 | 32.6 | 7.8 |
| 6 | 33.7 | 8.7 |
| 8 | 18.3 | 6.4 |
| 10 | 21.8 | 2.9 |
| 19 | 31.6 | 2.5 |
| 20 | 8.10 | 0.47 |
| 21 | 26.3 | 2.6 |

Results of the pharmacological study are given below

1) Pharmacokinetic study

Rabbits were injected with the polymer A, obtained in Example 5, in the form of a solution at a concentration of 8.64 gI/100 ml during 120 s, and with Hexabrix (solution of sodium and methylglucamine salts of ioxaglic acid) diluted to 8.64 gI/100 ml during 90 s.

The amounts injected correspond to 150 mgI/kg.

The plasma levels are recorded in FIGURE I. They demonstrate the persistence of a markedly higher iodine level with the polymer than with Hexabrix.

2) Urinary and biliary excretion

The results concerning urinary excretion, compared with those for Hexabrix, are given in Table II below:

Percentage urinary excretion values with time in rabbits.

TABLE II

| | Time (min) | Hexabrix % dose excreted | Polymer A % dose excreted |
|---|---|---|---|
| Urinary | 0–30 | 30.63 ± 6.99 | 9.91 ± 6.43 |
| Excretion | 30–120 | 45.76 ± 8.33 | 21.75 ± 7.40 |
| | 120–240 | 49.39 ± 12.25 | 30.24 ± 0.14 |

The polymer A is excreted via the urine. In contrast, biliary excretion is virtually nil.

3) Osmolarity

Osmolarity is known to be a critical parameter from the standpoint of side effects.

Results relating to the polymers thus prepared are given below

| Example | Osmolarity mOsm/kg (20° C.) |
|---|---|
| 5 | 489 |
| 6 | 559 |
| 10 | 43 |

-continued

| Example | Osmolarity mOsm/kg (20° C.) |
|---|---|
| | (+ NaCl 487) |
| 19 | 188 |
| 20 | 60 |
| 21 | 106 |
| | (37° C.) |

These results demonstrate osmolarity values which are acceptable and which are (sic) even lower than for plasma in the case of polymers containing an ester bridge or containing a bridge derived from epichlorohydrin.

The subject of the present invention is also contrast media which comprise at least one iodinated polymer as defined above.

These contrast media are usable in man and animals for radiological purposes.

The preferred pharmaceutical dosage form of the contrast media according to the invention consists of aqueous solutions of the polymers.

An example of a contrast medium according to the present invention is given below

| Contrast medium | |
|---|---|
| Polymer of Example 10 | 20 g |
| Water for injections Q.S. | 100 ml |

Generally speaking, the contrast media according to the invention may be administered by all routes traditionally used for contrast media, and especially parenterally (intravenously, intra-arterially, intra- or perilymphatically or by the subarachnoid route (myelography)) and orally.

The contrast media according to the present invention may be used, in particular, in angiography. They can generally be injected into man at iodine doses of 30 to 500 mgI/kg.

We claim:

1. A water soluble iodinated polymer comprising a dextran backbone having grafted thereon groups of the formula

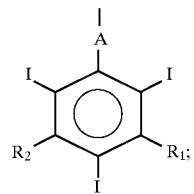

wherein

A is a group forming a bridge between the dextran backbone and the benzene ring;

$R_1$ is —COOH, —COOH salified with a pharmaceutically acceptable base,

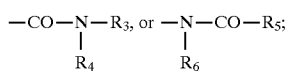

and
R$_2$ is

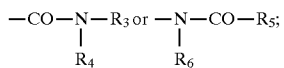

in which
R$_3$ is C$_{1-6}$ alkyl, C$_{1-6}$ hydroxyalkyl, C$_{1-6}$ polyhydroxyalkyl, C$_{1-6}$ alkoxy C$_{1-6}$ alkyl, C$_{1-6}$ alkoxy C$_{1-6}$ hydroxyalkyl or

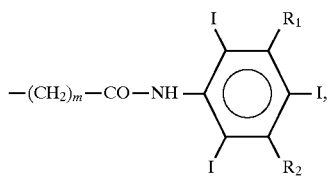

m being an integer from 1 to 6 and R$_1$ and R$_2$ having the same meanings as above;
R$_4$ and R$_6$ are independently hydrogen, C$_{1-6}$ alkyl, C$_{1-6}$ hydroxyalkyl, C$_{1-6}$ polyhydroxyalkyl, C$_{1-6}$ alkoxy C$_{1-6}$ alkyl, or C$_{1-6}$ alkoxy C$_{1-6}$ hydroxyalkyl; and
R$_5$ is C$_{1-6}$ alkyl, C$_{1-6}$ hydroxyalkyl, C$_{1-6}$ polyhydroxyalkyl, C$_{1-6}$ alkoxy C$_{1-6}$ alkyl, or C$_{1-6}$ alkoxy C$_{1-6}$ hydroxyalkyl.

2. Polymer according to claim 1,

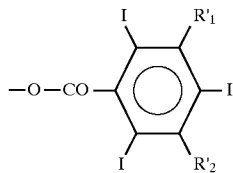

wherein A is —O—CO—, and wherein R$_1$ is R'$_1$ and R$_2$ is R'$_2$, in which
R'$_1$ and R'$_2$ are

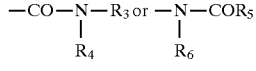

R$_3$, R$_4$, R$_5$ and R$_6$ having the meanings given in claim 1.

3. Process for preparing a polymer according to claim 2, comprising reacting an acid chloride of formula

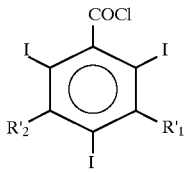

with a dextran in a polar solvent, R'$_1$ and R'$_2$ having the meaning given in claim 2.

4. Polymer according to claim 1, wherein A is —X—(CH$_2$)$_n$—CO—NH—, R$_1$ is R'$_1$ and R$_2$ is R"$_2$, in which n is an integer from 1 to 5, R"$_1$ is a —COOH group, a —COOH group salified with a pharmaceutically acceptable base or

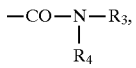

R"$_2$ is

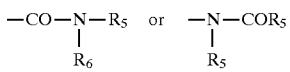

R$_3$, R$_4$, R$_5$ and R$_6$ having the meanings given in claim 1, and X is a group chosen from >N—, —NH—, —O—CH$_2$—CO—NH—,
—O—CH$_2$—CH—CH$_2$—NH— and
          |
          OH
—OCOCH$_2$—CH$_2$—CO—NH—.

5. Process for preparing a polymer according to claim 4 in which X is an >N— group, comprising reacting sodium periodate with a dextran to produce a dialdehydrodextran, and then reacting an amine of formula

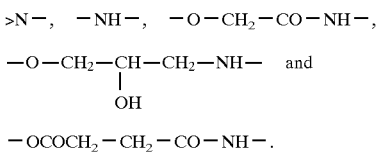

in which n, R"$_1$ and R"$_2$ have the meaning given in claim 4, with said dialdehydrodextran, and treating the resulting compound with a reducing agent.

6. Process for preparing a polymer according to claim 4 in which X is an —NH— group, comprising reacting mesyl chloride with a dextran at a temperature ranging from 70° C. to 100° C. to produce a mesylated dextran, and then reacting at about 65° C. for at least 6 hours an amine of formula

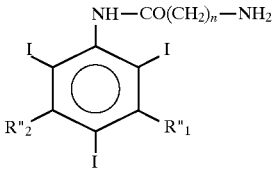

in which n, R"$_1$ and R"$_2$ have the meaning given in claim 4, with said mesylated dextran.

7. Process for preparing a polymer according to claim 4 in which X is an

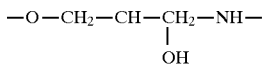

group, comprising reacting epichlorohydrin in an alkaline medium or epichlorohydrin in the presence of Zn(BF$_4$)$_2$ with a dextran to produce an epichlorohydrinated dextran, and then reacting an amine of formula

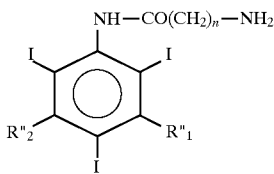

in which n, R"$_1$ and R"$_2$ have the meaning given in claim 4, with said epichlorohydrinated dextran.

8. Process for preparing a polymer according to claim 4 in which X is an —O—CO—CH$_2$—CH$_2$—CO—NH— group, comprising reacting succinic anhydride with a dextran in a polar solvent, using 4-dimethyl-aminopyridine as an acylation catalyst, to produce an activated polymer, and then reacting an amine of formula

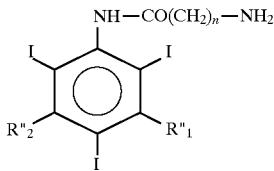

in which n, R"$_1$ and R"$_2$ have the meaning given in claim 4, with said activated polymer.

9. Polymer according to claim 1, wherein A is

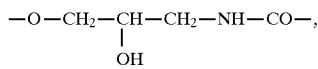

and wherein R$_1$ is R'$_1$ and R$_2$ is R'$_2$, in which

R'$_1$ and R'$_2$ are

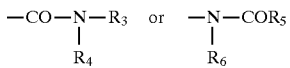

R$_3$, R$_4$, R$_5$ and R$_6$ having the meanings given in claim 1.

10. Process for preparing a polymer according to claim 9, comprising reacting epichlorohydrin in the presence of Zn(BF$_4$)$_2$ at about 80° C. with dextran for at least 4 hours to produce a chlorinated polymer, next reacting the chlorinated polymer with an ammonia solution at about 40° C. for at least 24 hours, to produce an aminated polymer, and then reacting at about 60° C. in the presence of triethylamine an acid chloride of formula

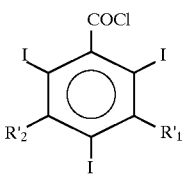

for at least 4 hours, R'$_1$ and R'$_2$ having the meaning given in claim 9, with the aminated polymer.

11. Contrast medium for radiography, comprising in an aqueous solution of a polymer according claim 1.

12. Contrast medium according to claim 11, in which the dextran has a molecular weight of 3,000 to 150,000.

13. Contrast medium according to claim 11, in which the dextran has a molecular weight of 10,000 to 100,000.

14. Polymer according to claim 1, in which the dextran has a molecular weight of 3,000 to 150,000.

15. Polymer according to claim 1, in which the dextran has a molecular weight of 10,000 to 100,000.

* * * * *